US012605137B2

(12) United States Patent
Dai et al.

(10) Patent No.: US 12,605,137 B2
(45) Date of Patent: Apr. 21, 2026

(54) VOLUME MANAGEMENT APPARATUS, DEVICE, AND STORAGE MEDIUM FOR EMERGENCY TREATMENT

(71) Applicant: SHENZHEN PEOPLES HOSPITAL, Shenzhen (CN)

(72) Inventors: Zhongliang Dai, Shenzhen (CN); Miao Lin, Shenzhen (CN)

(73) Assignee: SHENZHEN PEOPLES HOSPITAL, Shenzhen (CN)

( * ) Notice: Subject to any disclaimer, the term of this patent is extended or adjusted under 35 U.S.C. 154(b) by 3 days.

(21) Appl. No.: 18/576,565

(22) PCT Filed: Jul. 5, 2022

(86) PCT No.: PCT/CN2022/103900
§ 371 (c)(1),
(2) Date: Jan. 4, 2024

(87) PCT Pub. No.: WO2023/280158
PCT Pub. Date: Jan. 12, 2023

(65) Prior Publication Data
US 2024/0245382 A1 Jul. 25, 2024

(30) Foreign Application Priority Data
Jul. 5, 2021 (CN) .......................... 202110758366.5

(51) Int. Cl.
*A61B 8/06* (2006.01)
*A61B 8/00* (2006.01)
(Continued)

(52) U.S. Cl.
CPC ............ *A61B 8/065* (2013.01); *A61B 8/5223* (2013.01); *G06T 7/0012* (2013.01); *G06T 7/62* (2017.01);
(Continued)

(58) Field of Classification Search
CPC ..... A61B 8/065; A61B 8/5223; A61B 8/0883; G06T 7/0012; G06T 7/62;
(Continued)

(56) References Cited

U.S. PATENT DOCUMENTS

2017/0011515 A1* 1/2017 Liu ...................... A61B 8/5223
2019/0167188 A1* 6/2019 Gifford, III .............. A61B 8/12
(Continued)

OTHER PUBLICATIONS

Koratala, Abhilash, "Focused Cardiac Ultrasound for the Nephrologist: The Subxiphoid View" (Jan. 6, 2020), Renal Fellow Network: https://www.renalfellow.org/2020/01/06/focused-cardiac-ultrasound-for-the-nephrologist-the-subxiphoid-view/ (Year: 2020).*
(Continued)

*Primary Examiner* — Kaitlyn E Sebastian
(74) *Attorney, Agent, or Firm* — HAUPTMAN HAM, LLP

(57) ABSTRACT

A volume management apparatus includes a cardiac evaluation unit configured to evaluate whether the patient suffers from an organic heart disease based on an image of apical four chamber view; a parameter determination unit configured to determine a maximum inner diameter of inferior vena cava and a collapse rate of inferior vena cava based on an image of subxiphoid inferior vena cava view; a score calculation unit configured to determine scores that correspond to the LVEF value, the maximum diameter of the inferior vena cava, and the collapse rate of the inferior vena cava, respectively; and a fluid management plan determination unit configured to search for a fluid management plan corresponding to a score determined, and to perform volume management for the patient according to the fluid management plan searched.

9 Claims, 3 Drawing Sheets

(51) Int. Cl.

| | | |
|---|---|---|
| *A61B 8/08* | (2006.01) | |
| *G06T 7/00* | (2017.01) | |
| *G06T 7/62* | (2017.01) | |
| *G16H 20/17* | (2018.01) | |

(52) U.S. Cl.
CPC ... *G16H 20/17* (2018.01); *G06T 2207/30048* (2013.01); *G06T 2207/30104* (2013.01)

(58) Field of Classification Search
CPC .......... G06T 2207/30048; G06T 2207/30104; G16H 20/17; G16H 30/40; G16H 50/30
See application file for complete search history.

(56) References Cited

U.S. PATENT DOCUMENTS

| | | | | |
|---|---|---|---|---|
| 2019/0298303 | A1* | 10/2019 | Bingley | .................... A61B 8/54 |
| 2021/0169408 | A1* | 6/2021 | Levin | ..................... G16H 20/17 |
| 2021/0259664 | A1* | 8/2021 | Hare, II | ................. G06N 3/047 |

OTHER PUBLICATIONS

International Search Report and Written Opinion issued in International Application No. PCT/CN2022/103900; mailed Oct. 10, 2022; 12 pgs.

* cited by examiner

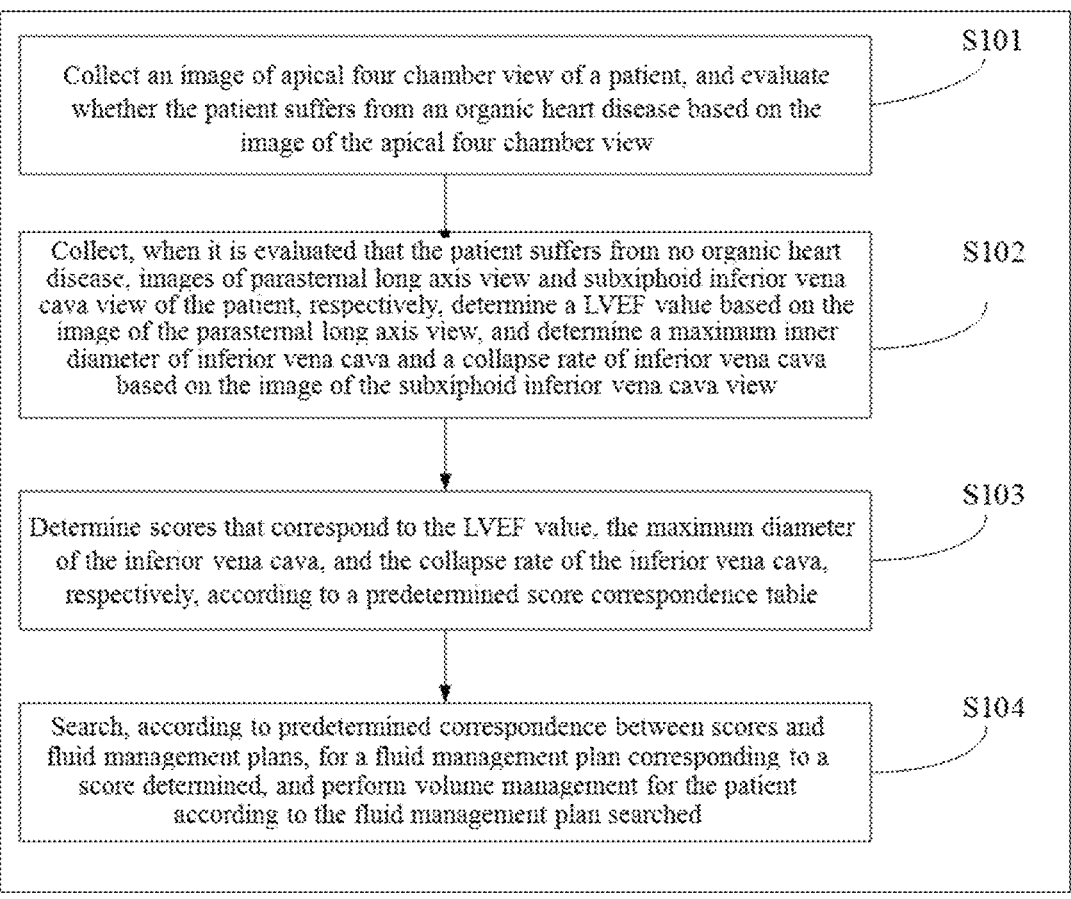

Collect an image of apical four chamber view of a patient, and evaluate whether the patient suffers from an organic heart disease based on the image of the apical four chamber view — S101

Collect, when it is evaluated that the patient suffers from no organic heart disease, images of parasternal long axis view and subxiphoid inferior vena cava view of the patient, respectively, determine a LVEF value based on the image of the parasternal long axis view, and determine a maximum inner diameter of inferior vena cava and a collapse rate of inferior vena cava based on the image of the subxiphoid inferior vena cava view — S102

Determine scores that correspond to the LVEF value, the maximum diameter of the inferior vena cava, and the collapse rate of the inferior vena cava, respectively, according to a predetermined score correspondence table — S103

Search, according to predetermined correspondence between scores and fluid management plans, for a fluid management plan corresponding to a score determined, and perform volume management for the patient according to the fluid management plan searched — S104

Fig. 1

| LVEF | Score of Left Ventricular Ejection Fraction (LVEF) value |
|---|---|
| <55% | 1 |
| 55%~70% | 2 |
| >70% | 3 |

Fig. 2

| Inner Diameter of (cm) Inferior Vena Cava | Collapse Rate of Inferior Vena Cava | Score of Inferior Vena Cava View |
|---|---|---|
| >2.1 | <50% | 0 |
| 1.5~2.1 | <50% | 1 |
| 1.5~2.1 | ≥50% | 2 |
| <1.5 | ≥50% | 3 |

Fig. 3

| Total Score | Fluid Management (within 30 min) |
|---|---|
| 1 | Supplement fluid by caution, and perform FAST ultrasound estimation |
| 2 | Supplement crystalloid fluid slowly with 5 ml · $kg^{-1}$ · $h^{-1}$ |
| 3~4 | Supplement crystalloid fluid quickly with 10 ml · $kg^{-1}$ · $h^{-1}$ |
| 5 | Supplement colloid fluid quickly with 10 ml · $kg^{-1}$ · $h^{-1}$ |
| 6 | Probably in an early state of shock, and perform FAST ultrasound estimation to determine whether blood transfusion is required |

VOLUME MANAGEMENT APPARATUS, DEVICE, AND STORAGE MEDIUM FOR EMERGENCY TREATMENT

CROSS-REFERENCE TO RELATED APPLICATION

The present disclosure is a U.S. National Phase of International Application Number PCT/CN2022/103900 filed Jul. 5, 2022, which claims priority to Chinese Patent Application No 202110758366.5, filed on Jul. 5, 2021, with the title "Volume management apparatus, device, and storage medium for emergency treatment", the contents of which are incorporated herein by reference in its entirety.

TECHNICAL FIELD

The present disclosure is related to the technical field of medical technology, and in particular relates to a volume management apparatus, device, and storage medium for emergency treatment.

BACKGROUND OF THE INVENTION

The number of patients who are admitted as emergency surgery are increasing due to the development of medical technology. During a medical operation, it is required to carry out volume supplementation for a patient based on his/her volume status. An appropriate volume supplement plan can provide sufficient volume preparation for the patient under an operation so as to reduce the loss of hemoglobin during the operation, lower the probability of blood transfusion and the risk of blood borne infections, and lower the incidence and mortality of postoperative complications of the patient. Excessive fluid supplement might cause damages to functions of multiple organs, such as the heart, lungs, brain, kidneys, and other organs that are more sensitive to fluid load. For elderly patients and those with poor cardiac function reserves, excessive fluid could even lead to death. Therefore, it is required to accurately know a volume of fluid demanded by the body of the patient and provide the patient with the supplementation with appropriate types and amounts of fluids.

At present, the commonly used volume estimation methods include traditional empirical method, volume load test method, passive leg raising test method, etc. Among them, the traditional empirical method estimates the patient's volume status by observing indicators such as mucosa color, skin elasticity, urine volume, urine color, blood pressure and heart rate. However, if the patient suffers from an unknown organic heart disease, empirical fluid supplementation might bring a fatal crisis to the patient. For the volume load test method, there is no standard definition with respect to the volume of fluid, which is not conducive to accurate determination of volume status of the patient. For the passive leg raising test method, it is not applicable in a scenario with relatively narrow space and limited time of operation. Therefore, there is an urgent need for a simple, efficient, safe, and accurate method for estimating a preoperative volume to meet operational needs of an emergency operation.

SUMMARY OF THE INVENTION

In view of these, the embodiments of the present disclosure provide a volume management apparatus, device, and storage medium for emergency treatment to solve the problems of low safety, being complex to operate, low efficiency, or low accuracy in volume estimation and management in the existing technology.

A first aspect of the present embodiment provides a volume management apparatus for emergency treatment, comprising:

a cardiac evaluation unit configured to collect an image of apical four chamber view of a patient, and evaluate whether the patient suffers from an organic heart disease based on the image of the apical four chamber view;

a parameter determination unit configured to collect, when it is evaluated that the patient suffers from no organic heart disease, images of parasternal long axis view and subxiphoid inferior vena cava view of the patient, respectively, determine a left ventricular ejection fraction (LVEF) value based on the image of the parasternal long axis view, and determine a maximum inner diameter of inferior vena cava and a collapse rate of inferior vena cava based on the image of the subxiphoid inferior vena cava view;

a score calculation unit configured to determine scores that correspond to the LVEF value, the maximum diameter of the inferior vena cava, and the collapse rate of the inferior vena cava, respectively, according to a predetermined score correspondence table; and a fluid management plan determination unit configured to search, according to predetermined correspondence between scores and fluid management plans, for a fluid management plan corresponding to a score determined, and perform volume management for the patient according to the fluid management plan searched.

Referring to the first aspect, in a first possible implementation of the first aspect, the cardiac evaluation unit is configured to collect the image of the apical four chamber view of the patient, determine a right heart to left heart ratio, blood flow direction, and valve morphology and function based on the image of the apical four chamber view, and determine whether the patient's heart suffers from an organic disease based on the right heart to left heart ratio, the blood flow direction, and the valve morphology and function.

Referring to the first aspect, in a second possible implementation of the first aspect, the score calculation unit is configured to search for a first score corresponding to the determined LVEF value according to a predetermined scoring table of LVEF values, and search for a second score corresponding to the determined maximum inner diameter and collapse rate of the inferior vena cava according to a predetermined scoring table of maximum inner diameters and collapse rates of the inferior vena cava.

Referring to the second possible implementation of the first aspect, in a third possible implementation of the first aspect, the predetermined scoring table of maximum inner diameters and collapse rates of the inferior vena cava includes that:

if a maximum inner diameter of the inferior vena cava>2.1 cm and a collapse rate of the inferior vena cava<50%, the second score is 0;

if a maximum inner diameter of the inferior vena cava is 1.5-2.1 cm and a collapse rate of the inferior vena cava<50%, the second score is 1;

if a maximum inner diameter of the inferior vena cava is 1.5-2.1 cm and a collapse rate of the inferior vena cava≥50%, the second score is 2; and if a maximum inner diameter of the inferior vena cava<1.5 cm and a collapse rate of the inferior vena cava≥50%, the second score is 3.

Referring to the second possible implementation of the first aspect, in a fourth possible implementation of the first aspect, the predetermined scoring table of LVEF values includes that:

if a LVEF value is less than 55%, then the first score is 1;

if a LVEF value is greater than or equal to 55% and less than 70%, then the first score is 2; and if a LVEF value is greater than or equal to 70%, then the first score is 3.

Referring to the second possible implementation of the first aspect, in a fifth possible implementation of the first aspect, the fluid management plan determination unit is configured to sum the first score and the second score that are searched for to determine a total score, and search for a fluid management plan corresponding to the patient according to predetermined correspondence between total scores and fluid management plans.

Referring to the fifth possible implementation of the first aspect, in a sixth possible implementation of the first aspect, the predetermined correspondence between total scores and fluid management plans includes:

when the total score is 1, selecting to perform Focused Assessment with Sonography in Trauma (FAST) ultrasound to estimate whether fluid supplementation is required;

when the total score is 2, selecting to supplement crystalloid fluid at a first preset speed;

when the total score is 3-4, selecting to supplement crystalloid fluid at a second preset speed, wherein the second preset speed is greater than the first preset speed;

when the total score is 5, selecting to supplement colloid fluid at a third preset speed, wherein the third preset speed is greater than the first preset speed; and when the total score is 6, selecting to perform FAST ultrasound to estimate whether blood transfusion is required.

Referring to the sixth possible implementation of the first aspect, in a seventh possible implementation of the first aspect, the first preset speed, the second preset speed, and the third preset speed are associated with a weight of the patient.

A second aspect of the embodiments of the present disclosure provides a volume management apparatus for emergency treatment, comprising a memory, a processor, and a computer program stored in the memory and capable of running on the processor, when the processor executes the computer program, a method implemented thereby comprises units that are compartmentalized by the apparatus according to any one of the first aspect.

A third aspect of the embodiments of the present disclosure provides a computer-readable storage medium, on which a computer program is stored, when the computer program is executed by a processor, a method implemented thereby comprises units that are compartmentalized by the apparatus according to any one of the first aspect.

Comparing with the existing technology in the field, the beneficial effects of the embodiments of the present disclosure are that, by collecting the image of the apical four chamber heart view, screening for the patient for an organic heart disease can be performed in advance in the present disclosure, which can effectively avoid safety issues associated with fluid supplementation in case of the patient suffering from an organic heart disease. When the patient suffers from no organic heart disease, further images of the parasternal long axis view and the subxiphoid inferior vena cava view of the patient are collected; in conjunction with the predetermined scoring table, a score related to a state of the patient is searched for; according to the predetermined correspondence between scores and fluid management plans, a fluid management plan corresponding to the patient is accurately searched out for performing volume management, so that fluid supplementation can be implemented for the patient in a simple, efficient, accurate manner.

BRIEF DESCRIPTION OF THE DRAWINGS

In order to provide a clear explanation for the technical solutions in the embodiments of the present disclosure, the accompanying drawings that are required in the description of the embodiments or the prior art will be introduced briefly below. Apparently, the accompanying drawings in the following description only refer to some of the embodiments of the present disclosure. For those skilled in the art, other drawings can be obtained based on these drawings without any creative labor.

FIG. 1 is a flowchart of implementation processes of a volume management method for emergency treatment according to an embodiment of the present disclosure;

FIG. 2 is a table of correspondence between LVEF values and scores according to an embodiment of the present disclosure;

FIG. 3 is a table of correspondence between parameters of the inferior vena cava under xiphoid process and scores according to an embodiment of the present disclosure;

FIG. 4 is a table of correspondence between total scores and fluid management plans according to an embodiment of the present disclosure;

DETAILED DESCRIPTION OF THE EMBODIMENTS

Figure 5:
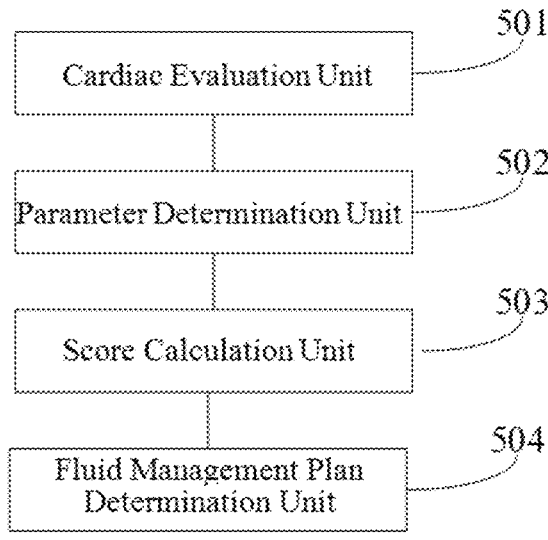
FIG. 5 is a schematic diagram of a volume management apparatus for emergency treatment according to an embodiment of the present disclosure.

In the following description, in order to thoroughly understand the embodiments of the present disclosure, the details such as specific system architecture, technology, and the like are provided for the purpose of illustration rather than limitation. However, it should be clear for those skilled in the art that the present disclosure can also be implemented in other embodiments without these specific details. In other cases, detailed descriptions of well-known systems, devices, circuits, and methods can be omitted to avoid confusion about the description of the present disclosure due to those unnecessary details.

To illustrate the technical solutions in the present disclosure, specific embodiments will be provided as following.

The purposes of supplementing a volume for a patient are to increase cardiac output, maintain tissue and organ perfusion, and improve tissue hypoxia. Appropriate volume supplementation can provide sufficient volume preparation for the patient under an operation so as to reduce the loss of hemoglobin during the operation, lower the probability of blood transfusion and the risk of blood borne infections, and lower the incidence and mortality of postoperative complications of the patient. Excessive fluid supplementation might cause damages to functions of multiple organs, such as the heart, lungs, brain, kidneys, and other organs that are more sensitive to fluid load. For elderly patients and those with poor cardiac function reserves, excessive fluid could even lead to death. Therefore, the significance of volume estimation lies in accurately estimating a volume status of the patient, knowing fluid requirement of the patient's body as accurately as possible, and providing the patient with the supplementation with the most appropriate types and amounts of fluids so as to improve the condition of the patient and lower medical costs.

At present, the commonly used volume estimation methods include a traditional empirical method, a volume load test, and a passive leg raising test (PLR).

The traditional empirical method involves estimation on a volume status of a patient by observing indicators such as mucosa color, skin elasticity, urine volume, urine color, blood pressure and heart rate, which is convenient, fast, and free of special procedures or additional costs and thus becomes the most commonly used method at present. However, when volume estimation is carried out by using this method, empirical fluid supplementation might bring a fatal crisis to the patient if the patient suffers from an unknown organic heart disease.

The volume load test involves application of a small dose of fluid for testing a response to a volume. However, there has been no consensus so far on how much a specific amount of the small dose of fluid should be, so it is not possible to accurately and effectively perform volume estimation.

The PLR test involves raising both lower limbs of a patient by 45 degrees to allow approximately 300 ml of effective circulating blood to return to the heart and maintain for several minutes, which is applicable for patients who suffer from heart and kidney injury and may have volume overload. However, due to relatively narrow emergency operation tables, limited preoperative operating time, and the need of collaborative estimation in conjunction with other testing approaches, the PLR might not be applicable to volume estimation in an emergency general anesthesia operation.

In case of a critically ill patient or a major operation, invasive procedures such as Central Venous Pressure (CVP) and Pulse Indicator Continuous Cardiac Output (PiCCO) measurement and monitor techniques are also applied sometimes.

The CVP refers to a pressure at where the superior and inferior vena cava enter the right atrium, which can be measured by placing a central venous catheter. However, due to the fact that the CVP can represent only the right heart preload but is not sufficient for the left heart volume, and that the CVP is affected by various factors such as intrathoracic pressure, vascular compliance, and valve regurgitation, the accuracy of fluid supplementation guided by the CVP has also been questioned.

The PiCCO measurement combines a transpulmonary thermodilution method and arterial pulse contour analysis, which can monitor on all aspects of the heart function, pulmonary liquid status, and hemodynamics of a patient. However, it is not applicable to an emergency operation due to limitations such as high costs and invasive procedures.

In view of these, an embodiment of the present disclosure provides a simple, efficient, accurate, and safe volume estimation method, i.e., a preoperative ultrasound estimation method using Dai's scoring method originated from medical school in Shenzhen City in the present disclosure, in which a possible hidden disease of a patient can be effectively excluded by collecting ultrasound images of the patient. Then, a score related to the patient is determined by acquiring, based on the ultrasound images, a left ventricular ejection fraction (LVEF) value, a maximum inner diameter of the inferior vena cava, and a collapse rate of the inferior vena cava during inhalation. Based on the determined score, a personalized fluid supplement strategy is searched for so as to provide simple, efficient, safe, and accurate fluid supplementation for the patient. Specific explanation is set forth below in conduction with the figures.

FIG. 1 is a schematic diagram of the implementation processes of a volume management method for emergency treatment provided by an embodiment of the present disclosure, the specific description of which is as following.

In S101, an image of apical four chamber view of a patient are collected, and estimation about whether the patient suffers from an organic heart disease is performed based on the image of the apical four chamber view.

In this case, the image of the apical four chamber view of the patient can be obtained using a perioperative transthoracic echocardiography image.

Transthoracic echocardiography examination may include parasternal long axis view, parasternal short axis view, apical four chamber heart view, subxiphoid four chamber view, and subxiphoid inferior vena cava view, among which, the parasternal long axis view can evaluate left ventricular systolic and diastolic function, measure the sizes of the left atrium, left ventricle, mitral valve, and aortic valve, calculate the ejection fraction (LVEF), exclude the possibility of pathology such as valve vegetation or valve prolapse, and observe the presence of pericardial effusion;

the parasternal short axis view (mainly referring to the middle segment of the ventricle) is the best location to evaluate segmental movement of the left ventricular wall and overall systolic function of the left ventricle. If a volume is relatively insufficient, the parasternal short axis view may present a "kissing sign" (i.e., the two papillary muscles are close or touching during contraction);

the apical four chamber view, also known as the apical four chamber ultrasound view or the apical four chamber section, can be used to evaluate anatomical morphology, function, and valve regurgitation of the mitral and tricuspid valves, identify pericardial effusion, evaluate the sizes of the right heart and left heart and a ratio of the right heart to the left heart, and overall left ventricular systolic function;

the subxiphoid four chamber view is a good location for evaluating pericardial effusion, which has good significance for diagnosing pericardial tamponade and can also determine whether there is an atrial septal defect or ventricular septal defect; and the subxiphoid inferior vena cava view can estimate a right atrial pressure and a central venous pressure, determine volume responsiveness and volume status, exclude the possibility of pericardial tamponade, and provide guidance for fluid treatment.

For the apical four chamber view, it can be used to:

1. observe inner diameters and volumes of the atrium (in systole) and the ventricle (in diastole), thicknesses and movements of the interventricular septum and the lateral walls of the left and right ventricles (in diastole).

2. determine whether atrioventricular connection condition is normal, and observe continuities of the interventricular septum and the interatrial septum.

3. measure a distance between attachment positions of the septal tricuspid valve and the anterior mitral leaflet, and observe for abnormalities in the atrioventricular valves.

4. determine the location, size, and movement of a tumor and thrombi in a chamber of each atrium or ventricular.

5. observe the morphology, pathway, and number of pulmonary veins for any abnormalities.
6. evaluate left ventricular wall motion and left ventricular heart function, and determine whether there is the formation of left ventricular wall aneurysm.

If it is evaluated by using the apical four chamber view that a patient suffers from an organic heart disease, including segmental wall motion abnormality, right heart function, the presence of pericardial effusion, and severe valve blood regurgitation, etc., reminder information can be generated timely, and it is possible to turn to other methods for volume estimation and volume management, instead of the preoperative ultrasound estimation method using Dai's scoring method originated from medical school in Shenzhen City in the present disclosure.

In a possible implementation, it is not limited to adopting the image of the apical four chamber view, but other ultrasound images, such as the parasternal short axis view, can also be included so that a more accurate estimation on whether the patient suffers from an organic heart disease can be obtained through comprehensive evaluations.

In S102, when it is evaluated that the patient suffers from no organic heart disease, images of the parasternal long axis view and the subxiphoid inferior vena cava view of the patient are collected, respectively. A left ventricular ejection fraction (LVEF) value is determined based on the image of the parasternal long axis view, and a maximum inner diameter of the inferior vena cava and a collapse rate of the inferior vena cava are determined based on the image of the subxiphoid inferior vena cava view.

When the patient has passed the evaluation regarding organic heart diseases, that is, when it is determined that the patient suffers from no organic heart disease, current scoring information of the patient can be further determined through ultrasound images, and volume estimation and management can be performed based on the scoring information.

During determination of the patient's scoring information, the left ventricular ejection fraction (LVEF) value can be determined using the image of the parasternal long axis view of the patient, and the maximum inner diameter and the collapse rate of the inferior vena cava can be determined using the image of the subxiphoid inferior vena cava view.

In S103, according to a predetermined score correspondence table, scores that correspond to the LVEF value, the maximum diameter of the inferior vena cava, and the collapse rate of the inferior vena cava are determined, respectively.

By using the image of the parasternal long axis view of the patient, the LVEF value is determined, so that a LVEF value related to the patient can be searched for according to a predetermined correspondence table of LVEF values vs. scores.

In the correspondence table of LVEF values vs. scores shown in FIG. 2, a first score that is related can be found according to the LVEF value. For example, in the case that the LVEF value is less than 55%, the first score is set as 1; in the case that the LVEF value is greater than or equal to 55% and less than 70%, then the first score is set as 2; in the case that the LVEF value is greater than or equal to 70%, then the first score is set as 3.

By using the image of the subxiphoid inferior vena cava view of the patient, the maximum inner diameter of the inferior vena cava is measured, and the collapse rate of the inferior vena cava during inhalation is calculated. In a score correspondence table of the subxiphoid inferior vena cava shown in FIG. 3, a related second score can be searched for according to the measured maximum inner diameter of the inferior vena cava and the collapse rate of the inferior vena cava.

For example, in the case that the maximum inner diameter of the inferior vena cava>2.1 cm and the collapse rate of the inferior vena cava<50%, the second score is set as 0; in the case that the maximum inner diameter of the inferior vena cava is 1.5-2.1 cm and the collapse rate of the inferior vena cava<50%, the second score is set as 1; in the case that the maximum inner diameter of the inferior vena cava is 1.5-2.1 cm and the collapse rate of the inferior vena cava is ≥50%, the second score is set as 2; and in the case that the maximum inner diameter of the inferior vena cava<1.5 cm and the collapse rate of the inferior vena cava is ≥50%, the second score is set as 3.

In S104, according to a predetermined correspondence between scores and fluid management plans, a fluid management plan corresponding to the determined score are searched for, and volume management are carried out for the patient according to the searched fluid management plan.

After determining the first score corresponding to the LVEF value as well as the second score corresponding to the maximum diameter and the collapse rate of the inferior vena cava, a summation between the first score and the second score can be performed to obtain a total score related to the patient. According to a predetermined correspondence table between total scores and fluid management plans, a fluid supplement plan related to the patient can be determined.

For example, in a possible implementation, when the total score is 1, FAST (Focused Assessment with Sonography in Trauma) ultrasound is selected to perform estimation on whether fluid supplementation is required, that is, in this case, determination for carrying out fluid supplementation or not depends on the estimation. The FAST ultrasound has been originally used to estimate the condition of abdominal bleeding of emergency patients, and later expanded to diagnose hemopneumothorax and pericardial effusion, which can accelerate the screening of patients in need of emergency treatment. After long-term clinical validation, the FAST is considered to have significant advantages in various aspects, such as determination of the presence of blood and fluid accumulation, parenchymal organ damage in the abdominal cavity, and large-scale field trauma treatment.

When the total score is 2, it is selected to supplement crystalloid fluid at a first preset speed. The first preset speed may be a speed slower than a second preset speed and a third preset speed.

When the total score is 3-4, it is selected to supplement crystalloid fluid at the second preset speed, the second preset speed being faster than the first preset speed.

When the total score is 5, it is selected to supplement colloid fluid at the third preset speed, the third preset speed being faster than the first preset speed.

In this case, the third preset speed can be the same as the second preset speed, or slower than the second preset speed, or faster than the second preset speed.

When the total score is 6, the patient is probably in an early state of shock then, and the FAST ultrasound can be selected to estimate whether blood transfusion is required.

FIG. 4 is a schematic diagram of total scores vs. fluid management plans provided by an embodiment of the present disclosure, as shown in FIG. 4. When the total score is 1, fluid supplementation should be carried out by caution, and the FAST ultrasound can be selected to estimate whether fluid supplementation is required. When the total score is 2, it is possible to supplement the crystalloid fluid in a slow manner, and a speed of supplementation of the crystalloid fluid can be 4-6 ml·kg$^{-1}$·h$^{-1}$, for example, 5 ml·kg$^{-1}$·h$^{-1}$ of FIG. 4, which means that for every 1 kg increase in the body weight of the patient, it needs to supplement 5 ml of the crystalloid fluid within one hour.

When the total score is 3-4, it is possible to supplement crystalloid fluid in a quick manner, and a speed of supplementation of the crystalloid fluid can 8-12 ml·kg$^{-1}$·h$^{-1}$, for example, 10 ml·kg$^{-1}$·h$^{-1}$ as shown in FIG. 4.

When the total score is 5, it is selected to perform quick supplementation with colloid fluid, and a speed of supplementation can be 8-12 ml·kg$^{-1}$·h$^{-1}$, for example, 10 ml·kg$^{-1}$·h$^{-1}$ as shown in FIG. 4.

When the total score is 6, the patient is probably in an early state of shock, and the FAST ultrasound is selected to estimate whether blood transfusion is required.

In this case, the crystalloid fluid can include Sodium Lactate Ringer's injection, and the colloid fluid can include of Hydroxyethyl Starch injection and Sodium Chloride injection, with a mass ratio of 130:0.4.

By collecting the image of the apical four chamber heart view, screening for the patient for an organic heart disease can be performed in advance in the present disclosure, which can effectively avoid safety issues associated with fluid supplementation in case of the patient suffering from an organic heart disease. When the patient suffers from no organic heart disease, further images of the parasternal long axis view and the subxiphoid inferior vena cava view of the patient are collected; in conjunction with the predetermined scoring table, a sore related to a state of the patient is search for; according to the predetermined correspondence between scores and fluid management plans, a fluid management plan corresponding to the patient is accurately searched out for performing volume management, so that fluid supplementation can be implemented for the patient in a simple, efficient, accurate manner.

In order to verify the volume management method for emergency treatment described in the embodiment of the present disclosure, the applicant has determined 60 patients for estimation in accordance with legal requirements in the condition that family members of the patients have obtained full informed consent, have understood the content of ultrasound estimation, have been explained with risks and privacy protection related issues, and have signed clinical trial informed consent forms and anesthesia informed consent forms. The patients are randomly divided into an empirical group and an ultrasound group by using a randomly generated number table. The empirical group refers to those applied with the traditional blood pressure and oxygen for preoperative volume estimation, and the ultrasound group refers to those applied with the ultrasound estimation method using Dai's scoring method originated from medical school in Shenzhen City as described in the present disclosure. The anesthesia for both the empirical group and the ultrasound group was performed by the same anesthesiologist.

The two groups of patients will complete the infusion of related fluid types and fluid volumes within 30 minutes. A medical record database is established for the patients of emergency operations, and SPSS 25.0 software is used for statistics correlated analysis and processing. Measurement data is expressed in a manner of mean±standard deviation. For inter group data comparison at the same time point, t-test for performing mean comparison between two samples is selected, so that comparison and analysis is performed on data at the same time point of the ultrasound group and the empirical group. For intra group data comparison at different time points, a variance analysis designed according to repeated measurements is selected. For count data, Chi-square test for R×C table is selected for comparison of constituent ratios. For hierarchy data, Wilcoxon rank sum test for comparing two independent samples is selected. According to a standard of $\alpha$=0.05, when P<0.05 serves as the difference, it is considered to be statistically significant. Comparison results obtained are as following.

With respect to a comparison of average arterial pressures between the empirical group and the ultrasound group at a time T2 in the beginning of operation, P*=0.003 and P<0.05, so the difference therebetween is statistically significant. An average arterial pressure of the ultrasound group at the beginning of operation is higher than that of the empirical group, and is closer to a value of normal blood pressure, so that the incidence of hypotension is lower for the ultrasound group. It is indicated that in an initial stage of operation, volume supplementation guided by Dai's method originated from medical school in Shenzhen City has a higher stability of blood pressure than that of the empirical method, and Dai's method originated from medical school in Shenzhen City can maintain hemodynamic stability during perioperative period.

In the study, with respect to a comparison of fluid types used by the patients of the empirical group and the ultrasound group within 30 minutes after selecting fluid supplement plans, P*=0.036, and according to the standard of $\alpha$=0.05, P*<0.05, so the difference with respect to fluid types used by the two groups of patients within 30 minutes after selecting the fluid supplement plans is statistically significant. For the empirical group, the anesthesiologist relies on his/her routine experience to observe mucosal color of eyelids and lips of the patient, palpate skin elasticity, and measure indicators such as blood pressure, heart rate, blood oxygen saturation so as to roughly determine volumes of the patients, and it is more inclined to perform crystalloid fluid supplement therapy for most of the patients in the initial stage. For the patients of the ultrasound group, after undergoing the ultrasound examination and the scoring-based plan selection, half of the patients in the group are arranged to undergone initial fluid supplementation that is 30 minutes after making a decision of "supplementing crystalloid fluid in a quick manner with 10 ml·kg$^{-1}$·h$^{-1}$"; the number of patients who is arranged to undergone initial fluid supplementation in accordance with "supplementing colloid fluid in a quick manner with 10 ml·kg$^{-1}$·h$^{-1}$" ranks the second; and four patients who are in a situation of "probably being an early shock state, undergoing FAST ultrasound estimation for determining whether blood transfusion is required" are additionally undergone real-time FAST estimation for determining whether blood transfusion is required, and evaluation of each of them by the chief anesthesiologist is that no infusion of blood product is required for now but quick peripheral venous infusion with colloid fluid can be applied to supplement the volume. However, with respect to a total fluid volume that the patients of each of the two groups are supplemented within 30 minutes after selecting the fluid supplement plans, P=0.134, so the difference between the groups has no statistical significance. With respect to comparisons of fluid types and fluid volumes during the whole time of operation, the two groups had similar situations, in which although the ultrasound group had a larger mean of total fluid volume, with respect to the comparison of constituent ratio of fluid types between the two groups, P=0.302, and with respect to the comparison of the mean of total fluid volume±standard deviation, P=0.085, so the differences each have no statistical significance. It is indicated that, for all of the patients, an impact of the ultrasound estimation on fluid usage mainly lies in selection of fluid types in the initial stage, but have no significant impact on the used fluid types and the total fluid volume that is injected throughout the operation.

With regard to an issue that the difference with respect to the fluid volume of supplementation within the 30 minutes has no statistical significance but the differences with respect to the fluid types of supplementation within 30 minutes as well as the average arterial pressure at the beginning of operation are statistically significant, it may be related to the fact that, compared to the empirical group, there are more patients who use the colloid fluid in the initial stage in the ultrasound group evaluated by the Dai's scoring method originated from medical school in Shenzhen City. Hydroxyethyl starch is an artificial colloid fluid synthesized from branched D-glucose polymers extracted from grains, has a low incidence of adverse conditions such as coagulation dysfunction, kidney damage, and allergic reactions, and further has the function of reducing inflammatory reactions, improving tissue hypoxia, and stabilizing capillary permeability, which has become an indispensable fluid therapy product in clinical practice [31,32]. The colloid fluid used in the study is hydroxyethyl starch 130/0.4 sodium chloride injection (i.e., Wanwen) of a 500 ml specification. For this study, the empirical group uses less Wanwen solution than the ultrasound group when formulating a fluid supplement plan before anesthesia induction. This can also be understood as that the crystalloid fluid should still be the first choice in case of resuscitation of non hemorrhagic shock in the concept of conventional experience estimation, and it is believed that the crystalloid fluid is safe for usage, has a precise effect on maintaining the balance of water and electrolyte in the human body, and is free of significant filtering load on organs, such as the kidneys. After the ultrasound estimation, the scoring and the selection of plan, on the one hand, there is the table about scores and fluid supplement plans for definite guidance, on the other hand, the anesthesiologist has known a cardiovascular volume of a current patient in a more intuitive and visualized manner by using the ultrasound, and thus is more confident in using the colloid fluid for volume expansion treatment. Also, it is possible for the patients of the ultrasound group to have more stable average arterial pressure at an immediate time of beginning of operation than that of the empirical group. After obtaining sufficient and appropriate volume supplementation, the blood pressures of the patients of the ultrasound group are slightly higher than that of their initial stage with insufficient volumes. That is, a drop of the blood pressure occurring in the ultrasound group is slighter in a period of time after use of anesthesia drugs, and an impact of the drugs on hemodynamics is increased. In the middle and later stages of operation (that are 30 minutes after selecting a fluid supplement plan), since it returns to autonomous fluid supplement control by the same anesthesia doctor, the differences with respect to the fluid types and the dosages of fluid supplementation between the two groups within a total time of operation have no statistical significance, respectively. It is thus indicated that application of the ultrasound estimation using Dai's scoring method originated from medical school in Shenzhen City has a better effect on stabilizing the average arterial pressure of the patients, can better reserve the preoperative volume for the patients, so that the patients are able to smoothly pass through the initial stage of operation.

It should be understood that the order of index numbers of respective steps in the above embodiment does not means to the order of execution. The order of execution of respective processes should be determined by their functions and internal logic, and should not constitute any limitation to the implementation process of the present embodiment.

FIG. 5 is a schematic diagram of a volume management apparatus for emergency treatment provided by an embodiment of the present disclosure, as shown in FIG. 5.

The apparatus comprises:

a cardiac evaluation unit 501, which is configured to collect an image of the apical four chamber view of a patient, and evaluate whether the patient suffers from an organic heart disease based on the image of the apical four chamber view;

a parameter determination unit 502, which is configured to collect, when it is evaluated that the patient suffers from no organic heart disease, images of the parasternal long axis view and the subxiphoid inferior vena cava view of the patient, respectively, determine a LVEF value based on the image of the parasternal long axis view, and determine a maximum inner diameter and a collapse rate of the inferior vena cava based on the image of the subxiphoid inferior vena cava view;

a score calculation unit 503, which is configured to determine scores that correspond to the LVEF value, the maximum diameter of the inferior vena cava, and the collapse rate of the inferior vena cava, respectively, according to a predetermined score correspondence table; and a fluid management plan determination unit 504, which is configured to search, according to predetermined correspondence between scores and fluid management plans, for a fluid management plan corresponding to a determined score, and carry out volume management for the patient according to the fluid management plan searched.

In a possible implementation, the cardiac evaluation unit is configured to collect the image of the apical four chamber view of the patient, determine a right heart to left heart ratio, blood flow direction, and valve morphology and function based on the image of the apical four chamber view, and determine whether the patient's heart suffers from an organic disease based on the right heart to left heart ratio, the blood flow direction, and the valve morphology and function.

In a possible implementation, the score calculation unit is configured to search for a first score corresponding to the determined LVEF value according to a predetermined scoring table of LVEF values, and search for a second score corresponding to the determined maximum inner diameter and collapse rate of the inferior vena cava according to a predetermined scoring table of maximum inner diameters and collapse rates of the inferior vena cava.

In a possible implementation, the predetermined scoring table of maximum inner diameters and collapse rates of the inferior vena cava includes that:

if a maximum inner diameter of the inferior vena cava>2.lcm and a collapse rate of the inferior vena cava<50%, the second score is set as 0;

if a maximum inner diameter of the inferior vena cava is 1.5-2.1 cm and a collapse rate of the inferior vena cava<50%, the second score is set as 1;

if a maximum inner diameter of the inferior vena cava is 1.5-2.1 cm and a collapse rate of the inferior vena cava≥50%, the second score is set as 2; and if a maximum inner diameter of the inferior vena cava<1.5 cm and a collapse rate of the inferior vena cava≥50%, the second score is set as 3.

In a possible implementation, the predetermined scoring table of LVEF values includes that:

if a LVEF value is less than 55%, then the first score is set as 1;

if a LVEF value is greater than or equal to 55% and less than 70%, then the first score is set as 2; and if a LVEF value is greater than or equal to 70%, then the first score is set as 3.

In a possible implementation, the fluid management plan determination unit is configured to sum the first score and the second score that are searched for to determine a total score, and search for a fluid management plan corresponding to the patient according to predetermined correspondence between total scores and fluid management plans.

In a possible implementation, the predetermined correspondence between total scores and fluid management plans includes that:

in the case that the total score is 1, it is selected to perform FAST ultrasound to estimate whether fluid supplementation is required;

in the case that the total score is 2, it is selected to supplement crystalloid fluid at a first preset speed;

in the case that the total score is 3-4, it is selected to supplement crystalloid fluid at a second preset speed, wherein the second preset speed is greater than the first preset speed;

in the case that the total score is 5, it is selected to supplement colloid fluid at a third preset speed, wherein the third preset speed is greater than the first preset speed; and in the case that the total score is 6, it is selected to perform FAST ultrasound to estimate whether blood transfusion is required.

In a possible implementation, the first preset speed, the second preset speed, and the third preset speed are associated with a weight of the patient.

The volume management apparatus for emergency department shown in FIG. 5 corresponds to the volume management method shown in FIG. 1.

Figure 6:
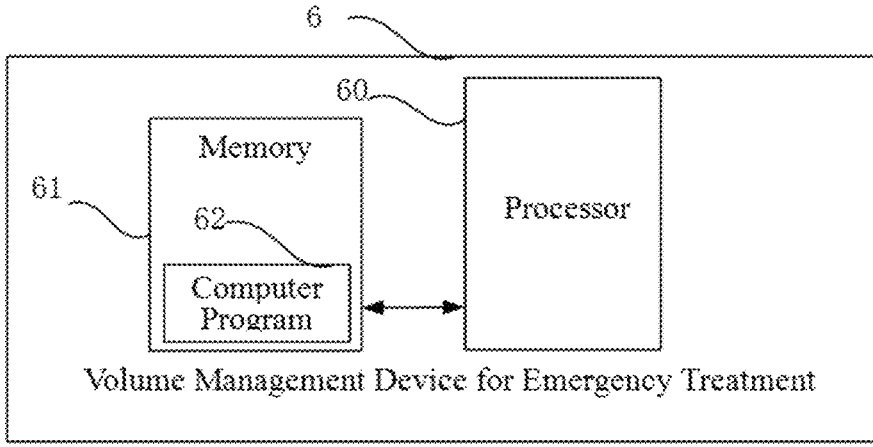
FIG. 6 is a schematic diagram of a volume management device for emergency treatment according to in an embodiment of the present disclosure.

FIG. 6 is a schematic diagram of a volume management device for emergency treatment provided by an embodiment of the present disclosure. As shown in FIG. 6, the volume management device 6 for emergency treatment in the present embodiment comprise: a processor 60, a memory 61, and a computer program 62 stored in the memory 61 and capable of running on the processor 60, e.g., a volume management program for emergency treatment. When executing the computer program 62, the processor 60 implements the steps of the volume management methods for emergency treatment as described above. Alternatively, when executing the computer program 62, the processor 60 implements the functions of respective modules/units in the apparatus as described in the aforementioned embodiments.

As an example, the computer program 62 can be divided into one or more modules/units, which are stored in the memory 61 and executed by the processor 60 to complete the present disclosure. The one or more modules/units can be a series of computer program instruction segments capable of performing specific functions, and the instruction segments are used to describe the execution process that the computer program 62 runs in the volume management device 6 for emergency treatment.

The volume management device for emergency treatment may include, but is not limited to, the processor 60 and the memory 61. It can be understood by those skilled in the art that FIG. 6 is only an example of the volume management device 6 for emergency treatment, but does not constitute a limitation to the volume management device 6 for emergency treatment. It is possible to include more or fewer components than those shown in the figure, combine certain components, or include different components. For example, the volume management device for emergency treatment can further include an input/output device, a network access device, a bus, etc.

The processor 60 may be a Central Processing Unit (CPU), and it can also be other general-purpose processors, Digital Signal Processors (DSPs), Application Specific Integrated Circuits (ASICs), Field Programmable Gate Arrays (FPGAs) or other programmable logic devices, discrete gates or transistor logic devices, discrete hardware components, etc. A general-purpose processor may be a microprocessor or any conventional processor.

The memory 61 may be an internal storage unit of the volume management device 6 for emergency treatment, such as a hard disk or memory of the volume management device 6 for emergency treatment. The memory 61 can also be an external storage device out of the volume management device 6 for emergency treatment, such as a plug-in hard disk, Smart Media Card (SMC), Secure Digital (SD) card, and Flash Card that are provided for the volume management device 6 for emergency treatment. Furthermore, the memory 61 can also include both the internal storage unit and the external storage device of the volume management device 6 for emergency treatment. The memory 61 is configured to store the computer program and other programs and data required by the volume management device for emergency treatment. The memory 61 can also be configured to temporarily store data that has been output or will be output.

It can be clearly understood by those skilled in the art that, for the convenience and conciseness of description, illustration of the present disclosure is presented only by taking various functional units and modules that are compartmentalized as above as an example. In practical applications, it is possible to assign the above functions to different functional units and modules as desired, that is, an internal construction of the device can be divided into different functional units or modules to complete all or part of the functions described above. The various functional units and modules in the embodiments can be integrated into one processing unit, or each of the various units/modules can be physically presented in an independent manner, or two or more units/modules can be integrated into one unit. These integrated units can be implemented in the form of hardware as well as software functional units. In addition, the specific names of various functional units and modules are only for the purpose of distinguishing them from each other, but not for limiting the scope of protection of the present disclosure. The specific working process of the units and modules in the device above can refer to that of the method in the foregoing process embodiments, which will not be described any further.

In the above embodiments, various embodiments have their own emphasis to be described. For the part that is not detailed or recorded in an embodiment, reference therefor can be made to the relevant descriptions of other embodiments.

It can be realized by those of ordinary skill in the art that the units and algorithm steps of each example described in the disclosed embodiments can be implemented by using electronic hardware or a combination of computer software and electronic hardware. Whether these functions are executed in hardware or software depends on the specific application and design constraints of the technical solution. For each specific application, a professional technician can use different methods to achieve the described functions, but such implementation should not be deemed to go beyond the scope of the present disclosure.

In the embodiments provided by the present disclosure, it should be understood that the disclosed apparatus/terminal device and method can be implemented in other ways. For example, the embodiments of apparatus/terminal device described above are only illustrative, for example, compartmentalization of modules or units is only a logical functional division, and there may be other division manners in actual implementation, such as a plurality of units or components being combined or integrated into another system, or some features being ignored or not executed. Further, coupling, direct coupling or communicative connection between each other that is displayed or discussed can be indirect coupling or communicative connection by means of some interfaces, devices or units, which can be in the electrical, mechanical or other forms.

The units described as separate components can be or may can be not physically separated, and the components displayed as one unit can be or can be not a physical unit, that is, they can be located in one place or distributed across multiple network units. Some or all of the units can be selected according to actual needs to achieve the purpose of the technical solution of the embodiment.

In addition, respective functional units in various embodiments of the present disclosure can be integrated into one processing unit, or each of the units can be physically presented in an independent manner, or two or more units can be integrated into one unit. These integrated units can be implemented in the form of hardware as well as software functional units The integrated modules/units, if implemented in the form of software functional units and sold or used as an independent product, can be stored in a computer-readable storage medium. Based on this understanding, it is also possible for the present disclosure to implement all or part of the processes in the above-mentioned embodiment through hardware related to computer program instructions. The computer program can be stored in a computer-readable storage medium, and the computer program, when executed by the processor, can implement the steps of the above-mentioned process embodiments. In this case, the computer program includes computer program codes, which may be in the form of source code, object code, executable file, or some intermediate form. The computer-readable medium may include: any entity or device capable of carrying the computer program codes, recording medium, USB flash drive, portable hard drive, magnetic disc, optical disc, computer memory, read-only memory (ROM), Random Access Memory (RAM), electrical carrier signal, telecommunication signal, and software distribution medium, etc. It should be noted that the items included in the computer-readable medium can be appropriately increased or decreased according to the requirements of legislation and patent practice in the jurisdiction. For example, in some jurisdictions, the computer-readable medium does not include the electrical carrier signal and the telecommunication signal according to legislation and patent practice.

The above embodiments are intent to provide illustration only for the technical solutions of the present disclosure, instead of limitation thereto. Although the present disclosure has been described in detail with reference to the above embodiments, it should be understand by those of ordinary skill in the art that modifications still can be made to the technical solutions described in the various foregoing embodiments, or equivalent replacements can still be made to some technical features thereof, and that the essence of the technical solutions related to these modifications or replacements do not deviate from the spirit and scope of the technical solutions of the embodiments of the present disclosure, and should be included in the scope of protection of the present disclosure.

The invention claimed is:

1. A volume management apparatus for use in the emergency treatment of a patient, comprising:

a cardiac evaluation unit provided in a processor, configured to collect an image of an apical four chamber view of the patient's heart, and use the collected image of the apical four chamber view to evaluate whether or not the patient suffers from an organic heart disease;

a parameter determination unit provided in the processor, configured to collect, when it is evaluated that the patient does not suffer from organic heart disease, images of both a parasternal long axis view and a subxiphoid inferior vena cava view of the patient's heart, respectively;

determining a left ventricular ejection fraction (LVEF) value based on the image of the parasternal long axis view;

determining a maximum inner diameter of the inferior vena cava and a collapse rate of the inferior vena cava based on the image of the subxiphoid inferior vena cava view;

a score calculation unit provided in the processor, configured to determine a total score that corresponds to a total of the individual scores for the LVEF value, the maximum diameter of the inferior vena cava, and the collapse rate of the inferior vena cava, respectively, according to a predetermined score correspondence table;

a fluid management plan determination unit provided in the processor, configured to select, according to predetermined correspondence between the total score and a plurality of fluid management plans, a fluid management plan corresponding to the total score, and perform volume management for the patient according to the fluid management plan selected;

wherein the score calculation unit provided in the processor is configured to search for a first score corresponding to the determined LVEF value according to a predetermined scoring table of LVEF values, and to search for a second score corresponding to the determined maximum inner diameter and collapse rate of the inferior vena cava according to a predetermined scoring table of maximum inner diameters and collapse rates of the inferior vena cava.

2. The volume management apparatus according to claim 1, wherein the cardiac evaluation unit provided in the processor is configured to collect the image of the apical four chamber view of the patient, determine a right heart to left heart ratio by measuring an internal diameter of a right ventricle and an internal diameter of a left ventricle, analyzing blood flow direction, and assessing valve morphology and function based on the image of the apical four chamber view, and determine whether the patient's heart suffers from an organic disease based on the right heart to left heart ratio, the blood flow direction, and the valve morphology and function.

3. The volume management apparatus according to claim 1, wherein the predetermined scoring table of maximum inner diameters and collapse rates of the inferior vena cava includes that:

if a maximum inner diameter of the inferior vena cava>2.1 cm and a collapse rate of the inferior vena cava<50%, the second score is 0;

if a maximum inner diameter of the inferior vena cava is 1.5-2.1 cm and a collapse rate of the inferior vena cava<50%, the second score is 1;

if a maximum inner diameter of the inferior vena cava is 1.5-2.1 cm and a collapse rate of the inferior vena cava≥50%, the second score is 2; and if a maximum inner diameter of the inferior vena cava<1.5 cm and a collapse rate of the inferior vena cava≥50%, the second score is 3.

4. The volume management apparatus according to claim 1, wherein the predetermined scoring table of LVEF values includes that:

if a LVEF value is less than 55%, then the first score is 1;

if a LVEF value is greater than or equal to 55% and less than 70%, then the first score is 2; and if a LVEF value is greater than or equal to 70%, then the first score is 3.

5. The volume management apparatus according to claim 1, wherein the fluid management plan determination unit provided in the processor is configured to sum the first score and the second score that are searched for to determine a total score, and search for a fluid management plan corresponding to the patient according to predetermined correspondence between total scores and fluid management plans.

6. The volume management apparatus according to claim 5, wherein the predetermined correspondence between total scores and fluid management plans includes:

when the total score is 1, selecting to perform Focused Assessment with Sonography in Trauma (FAST) ultrasound to estimate whether fluid supplementation is required;

when the total score is 2, selecting to supplement crystalloid fluid at a first preset speed;

when the total score is 3-4, selecting to supplement crystalloid fluid at a second preset speed, wherein the second preset speed is greater than the first preset speed;

when the total score is 5, selecting to supplement colloid fluid at a third preset speed, wherein the third preset speed is greater than the first preset speed; and when the total score is 6, selecting to perform FAST ultrasound to estimate whether blood transfusion is required.

7. The volume management apparatus according to claim 6, wherein the first preset speed, the second preset speed, and the third preset speed are associated with a weight of the patient.

8. A volume management device for emergency treatment comprising a memory, a processor, and a computer program stored in the memory and capable of running on the processor, wherein when the processor executes the computer program, a method implemented thereby comprises units that are compartmentalized by the apparatus according to claim 1.

9. A computer-readable storage medium, on which a computer program is stored, wherein when the computer program is executed by a processor, a method implemented thereby comprises units that are compartmentalized by the apparatus according to claim 1.

* * * * *